United States Patent
Cunningham

[19]

[11] Patent Number: 6,129,715
[45] Date of Patent: Oct. 10, 2000

[54] GUARD TO PROTECT MEDICAL APPLIANCE

[76] Inventor: Franklin D. R. Cunningham, 65 Valley Rd., Hampton, N.J. 08827

[21] Appl. No.: 09/080,526

[22] Filed: May 18, 1998

Related U.S. Application Data

[60] Provisional application No. 60/047,033, May 19, 1997.

[51] Int. Cl.[7] .................................. A61F 5/44; A61F 5/48
[52] U.S. Cl. .......................... 604/332; 604/337; 604/345; 604/338; 604/351; 604/353; 128/885
[58] Field of Search ................................ 604/332, 385.1, 604/385.2, 337, 345, 338, 351, 353; 128/885

[56] References Cited

U.S. PATENT DOCUMENTS

| | | |
|---|---|---|
| 260,561 | 7/1882 | French . |
| 1,922,763 | 8/1933 | Gricks . |
| 2,129,054 | 9/1938 | Geisler, Jr. . |
| 3,176,686 | 4/1965 | Barnes . |
| 3,503,392 | 3/1970 | Beeman . |
| 4,926,883 | 5/1990 | Strock . |
| 5,000,748 | 3/1991 | Fenton . |
| 5,072,738 | 12/1991 | Wonder et al. . |
| 5,167,240 | 12/1992 | Rozier et al. . |
| 5,178,614 | 1/1993 | McDowell et al. . |
| 5,338,315 | 8/1994 | Baker . |
| 5,557,804 | 9/1996 | Ovortrup et al. . |

*Primary Examiner*—John G. Weiss
*Assistant Examiner*—Miley Craig Peppers, III
*Attorney, Agent, or Firm*—Synnestvedt & Lechner LLP

[57] ABSTRACT

Guard devices adapted to protect a medical appliance attached to and in communication with an opening in the body having:

- a rigid, substantially U-shaped base member extending in a base plane and including a pair of opposing side members extending along the length of the device, both sides members having ends that together define an opening in the base member;
- a plurality of spaced-apart rigid cross-members extending between the side members and upwardly from the base plane, with the base members and the cross-members cooperatively defining a cavity adapted to completely enclose the medial appliance;
- one or more rigid base members extending between two or more of the aforementioned members; and
- means for securing the base member to the body of the person, wherein the body has an opening with a medical appliance attached thereto in communication therewith, so that the medical appliance is completely enclosed by the cavity defined by the base member and the cross-member.

14 Claims, 2 Drawing Sheets

GUARD TO PROTECT MEDICAL APPLIANCE

CROSS-REFERENCE TO RELATED APPLICATION

The present application claims priority benefit of U.S. Provisional patent application Ser. No. 60/047,033 filed May 19, 1997, the disclosure of which is hereby incorporated herein by reference.

BACKGROUND OF THE INVENTION

The present invention relates to guard devices adapted to protect medical appliances attached to body openings. In particular, the present invention relates to guard devices in which braced spaced-apart cross-members extend between the side members of a U-shaped base member and upwardly from the plane of the base member to define a cavity that completely encloses the medical appliance. The present invention particularly relates to devices for the protection of ostomies having a stoma inserted therein in communication with a bag attached thereto.

Individuals having medical devices attached to openings in their body lack the confidence to participate in sports or other activities. The concern is that the appliance may detach from their body, or, even worse, on an impact or other external force may be applied to the appliance, resulting in an injurious complication. This is particularly a concern for ostomy patients who must exercise caution to prevent not only damage to their ostomy appliance, but also to their ostomy incision and the stoma inserted therein.

Shields have been designed to more comfortably secure ostomy appliances to the body, and to protect the incision and stoma from incidental contact. To date, however, there has not been devised a device that is sufficiently protective to permit ostomy patients, and wearers of other medical appliances, to have the confidence to engage in sports and activities involving even the slightest degree of exertion.

U.S. Pat. Nos. 1,922,763 and 2,129,054 disclose colostomy appliances having a wire support frame wherein the mouth of the colostomy bag engages the stoma at the colostomy. However, the wire frame provides no protection to the colostomy bag against impact and other external forces.

U.S. Pat. No. 5,338,315 discloses another colostomy protection device having a semi-rigid guard covering and protecting the stoma. Again, only the stoma is protected, the colostomy bag is permitted to hang freely, and is not protected against impact and other external forces.

U.S. Pat. No. 5,178,614 discloses a shield that provides protection to both the colostomy stoma and the colostomy bag attached thereto. The shield, however, is a rigid thin shell that does not permit expansion of the colostomy bag as it fills. The shell retains heat, promoting the rapid growth of intestinal flora in the liquids contained in the colostomy bag. Additionally, there is no access to the colostomy bag from the bottom of the shield. The shield must be removed in order to empty the colostomy bag.

There remains a need for protective devices for colostomy bags and other medical appliances attached to openings in the body, which protect the appliance and secure it to the body, and permit access to the appliance without removal of the protective device. For appliances such as ostomy bags, there is a need for these protective devices to also permit the dissipation of body heat, to expand if the bag fills, and to allow drainage of the bag without removal of the protective device.

SUMMARY OF THE INVENTION

This need is met by the present invention. The present invention provides guard devices adapted to shield and protect from external pressures or impacts medical appliances that attach to an opening in the body. The guard devices address the problem of a patient's or physician's fear of injury to the body opening or damage to the medical appliance.

Therefore, according to one embodiment of the present invention, a guard device is provided adapted to protect a medical appliance attached to an opening in the body, wherein the device includes:

a rigid substantially U-shaped base member extending in a base plane, with the U-shaped base member including a pair of opposing side members extending along the length of the device, both side members having ends that together define an opening in the base member;

a plurality of spaced-apart rigid cross-members extending between the side members and upwardly from the base plane, with the base member and the cross members cooperatively defining a cavity adapted to completely enclose the medical appliance;

at least one rigid brace member extending between two or more of the aforementioned members; and Means for securing the base member to the body of a person, wherein the body has an opening with the medical appliance attached thereto, so that the medical appliance is completely enclosed by the cavity defined by the base member and the cross-members.

The cross-members are preferably equally spaced apart and extend the entire length of the side members. The preferred embodiment also employs a plurality of brace members. The means for securing the device to the body is typically a waist strap, such as a belt, but any equivalent securing means may be employed.

The guard device of the present invention allows individuals to engage in activities that otherwise may be limited to them because of the medical appliance they are wearing. In addition, it also provides the person with the confidence to participate in such activities without fear that the appliance will detach or be damaged, or that injury will occur at the site of appliance attachment. Guard devices in accordance with the present invention uniquely shield and protect while at the same time allowing mobility to the wearer but not further restricting that person's movements. Guard devices in accordance with the present invention are also unique in the way that they allow for access to medical appliances without having to remove the guard device.

A more complete appreciation of the invention and many other intended advantages can be readily obtained by reference to the following detailed description of the preferred embodiment and claims in conjunction with the accompanying drawings, which disclose the principals of the invention and the best modes which are presently contemplated for carrying them out.

DETAILED DESCRIPTION OF THE PREFERRED EMBODIMENTS

Figure 1:
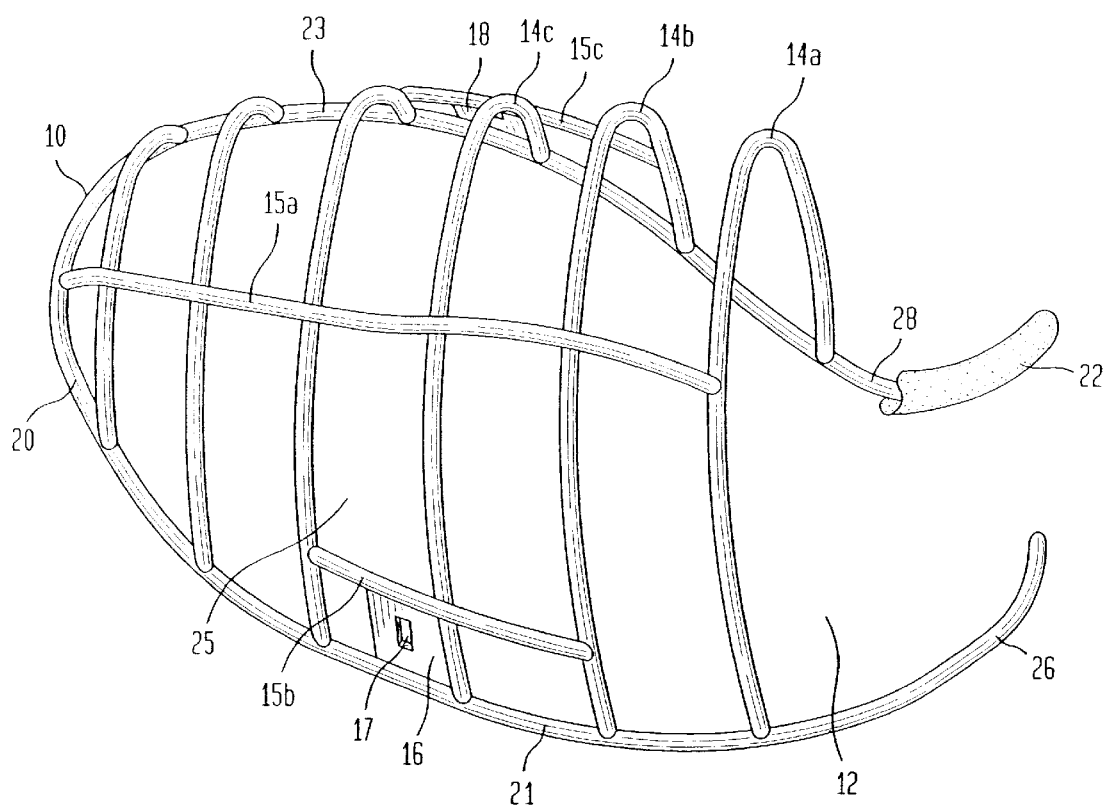
FIG. 1 is a side, perspective view of a device according to the present invention.
Figure 2:
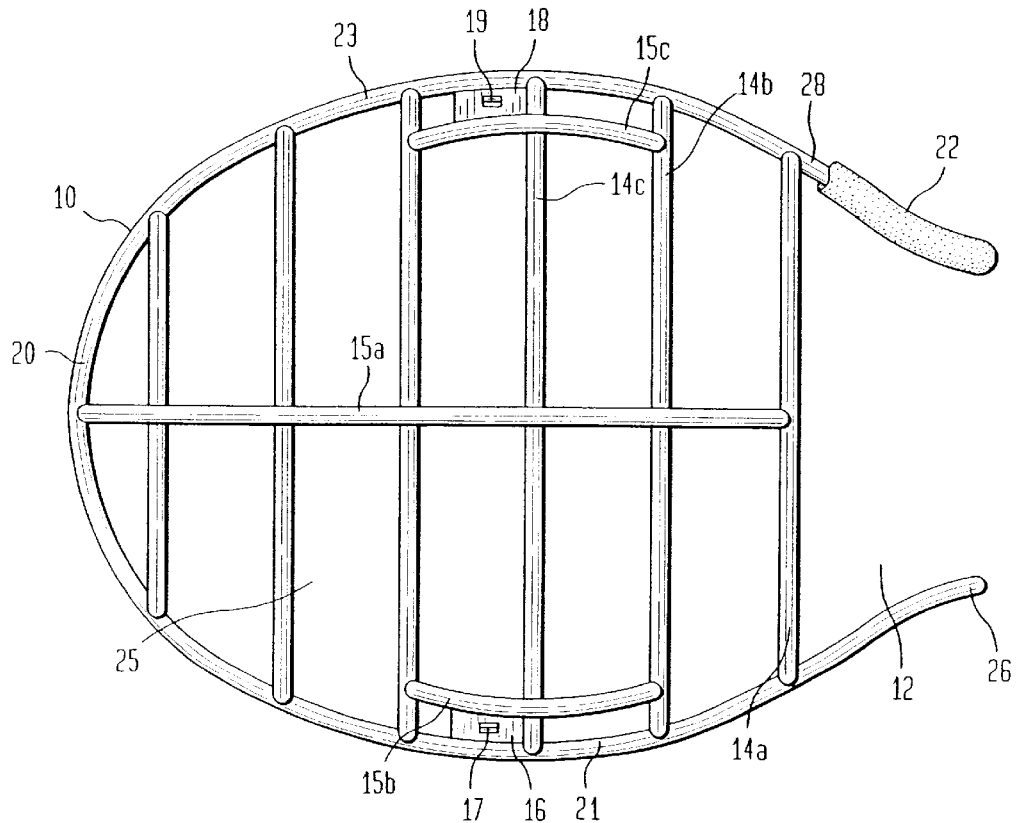
FIG. 2 is a top view of the device of FIG. 1.
Figure 3:
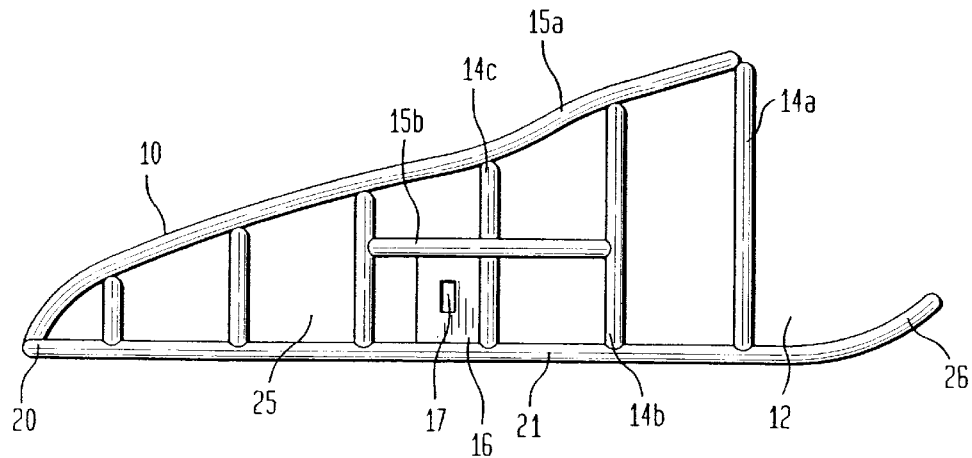
FIG. 3 is a side view of the device of FIG. 1.

Referring to FIGS. 1–3, guard device 10 has a U-shaped base member 20 defining an opening 12 and including a pair of opposing side members 21 and 23 extending along the length of guard device 10. Cross-members 14a, 14b, 14c, etc. extend between side members 21 and 23 and upwardly from base member 20, so that the base member 20 and cross-members cooperatively define a cavity 26 adapted to completely enclose a medical appliance (not shown).

Brace members 15a, 15b and 15c extend between the cross-members. Plate 16 is attached to base member 20, cross-member 14c and brace member 15b and plate 18 is attached to base member 20, cross-member 14c and brace member 15c. The plates 16 and 18 have openings 17 and 19, respectively, for the attachment of a waist strap (not shown).

The base member 20 may optionally have an elastomer coating 22 to frictionally secure the base member to the body. In the depicted embodiment, surgical tubing is employed, and was selected because it is non-irritating and non-toxic, and is used extensively in the medical profession.

The base member 20, cross-members 14a, 14b, 14c, etc., brace members 15a, 15b, 15c and plates 16 and 18 are preferably fabricated from metal and are preferably welded together. Other structural materials, such as high impact moldable plastics and composites, may be employed, provided that active use would not cause the material to shatter into sharp pieces that would damage the medical appliance or the area of the body to which the appliance is attached. The base member, cross-members, brace members and plates are preferably fabricated from ⅛ inch stainless steel, preferably Type 316L. The stainless steel provides extra strength and acts as a shock absorber in the event of an impact or other external pressure.

In the particular embodiment, the elastomer coating 22 is surgical tubing made of natural rubber with a ⅛ inch I.D. and ¹⁄₁₆ O.D. wall. Natural and synthetic elastomeric coatings may also be employed.

Referring to FIGS. 1 and 3, the side members 21 and 23 of the guard device have ends 26 and 28, respectively, that extend upwardly from base member 20. This is particularly useful with ostomy bags to prevent lateral movement of a bag when the patient is in motion. This feature also protects the drainage end of the bag from damage, as well as from the possible "pinching" of the bag. It should be noted that this is an optional feature that represents a preferred embodiment.

Opening 12 at the bottom of the guard device 10 does not restrict the patient's movements and allows for easy access to the medical appliance. For ostomy bags, this opening corresponds to the drainage path of the bag. When the bag needs to be drained, the drainage path on the bag is easily accessible. Cavity 25 defined by the contour of cross-members 14a, 14b, and 14c allows for expansion as the colostomy bag fills, while still affording the bag protection against impact or other external pressures.

Guard devices in accordance with the present invention completely enclose medical devices attached to body openings. The depicted example provides protection to a patient fitted with a colostomy bag, and is contoured to the shape and size of the bag. In addition to providing protection, this also prevents bag misalignment. The depicted embodiment is suitable for use with essentially any conventional ostomy appliance in the form of a flexible pouch or bag to be attached to the body of a patient to receive discharge from a stoma inserted as part of a colostomy, ileostomy, urostomy or ureterostomy procedure.

For colostomy appliances, the guard device of the present invention protects the stoma, the operated area, and the bag itself. A person can wear a belt with their clothing in lieu of elasticized waistbands or trousers with suspenders. The cross members and brace members permit the belt to be applied without crushing the medical appliance.

While many states exempt colostomy patients from state laws requiring the wearing of safety belts while driving, because of the tendency of safety belts to puncture colostomy bags, irritate the stoma area and cause separation of the colostomy bag from the stoma area. The guard device of the present invention permits a seat belt to be worn over the colostomy area, and absorbs external pressure created by sudden stopping or impacts from accidents. The guard device thus provides added safety and confidence to colostomy patient drivers. Because seat belts are also required on construction equipment, the guard device of the present invention also permits colostomy patients to operate heavy equipment.

Other construction workers such as masons benefit from the guard device of the present invention. The guard device prevents accidents such as punctures or irritation to the stoma area from contact with sharp edges, tools and other equipment.

However, the guard device of the present invention can be shaped into various sizes that conform to a patient's body or a physician's requirements. The guard device design is not limited to an oblong or oval design; any other geometric pattern may be suitable depending upon the desired application. When fabricated from metal, guard devices in accordance with the present invention may be constructed by bending and welding the metal surfaces to produce an object having the desired shape.

Preferred embodiments of the device depicted in FIGS. 1–3 employ equally spaced apart cross-members that more preferably extend along the entire length of the side members 21 and 23. The use of a plurality of brace members is also preferred. The described guard device employs a waist strap, such as a belt, to secure the device to the body. However, any equivalent means of securing such a device to the body may be employed, including hook and loop fasteners, adhesive films, straps around other portions of the body, and the like. The depicted device is easily removed by loosening or unhooking the waist strap.

In addition to ostomies, guard devices according to the present invention may also be used to protect medical appliances in communication with other surgically created openings, such as a heplock for the infusion of intravenous fluids, ports or tubes used for drug infusion or dialysis, or tubes for surgical drainage. The guard device may also be employed to protect a medical appliance in communication with a congenital orifice of the body, such as the mouth, nostrils, ears, anus, and the like.

This is particularly useful with patients who have contact with children or pets. It is normal for both children and pets to jump around, jump up on, bump into, fall against or lean on a person. Guard devices according to the present invention thus prevent impact damage to medical appliances in such situations. In addition, people who experience equilibrium problems have a tendency to "bump" into things and cause damage to medical appliances and operated areas. Guard devices according to the present invention serve to protect such delicate and tender areas of people with equilibrium problems.

The guard devices of the present invention provide the protection to surgical areas and medical appliances needed for individuals to enjoy light sports. For example, a baseball player, basketball player, fisherman, golfer, bowler, soccer player, horseback rider, dancer, bicyclist, motorcycle rider, and the like, may continue to participate in these activities with the confidence that their medical equipment or surgical areas will not be damages or abused by external forces. The guard device of the present invention is particularly well suited for the protection of medical appliances and the sites of attachment thereof with patients having impaired mental faculties who are at risk of tearing off or otherwise damaging the attached device.

Most importantly, the guard devices of the present invention serve to improve the quality of life of patients that must undergo surgery, particularly colostomy patients. It returns to the patients, in some measure, the enjoyment or pleasure of their normal life patterns.

The foregoing description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A guard device adapted to protect a medical appliance attached to and in communication with an opening in the body, said device comprising:

a rigid, substantially U-shaped base member extending in a base plane and including a pair of opposing side members extending along the length of said device, both side members having ends that together define an opening in said base member;

a plurality of spaced-apart rigid cross-members extending between said side members and upwardly from said base plane, said base member and said cross-members cooperatively defining a cavity adapted to completely enclose said medical appliance;

one or more rigid brace members extending between two or more of said members; and means for securing said base member to the body of a person, said body having an opening with a medical appliance attached thereto and in communication therewith, so that said medical appliance is completely enclosed by said cavity defined by said base member and said cross-members.

2. The device of claim 1, wherein said base member, said cross-members and said brace members are made of metal.

3. The device of claim 2, wherein said metal is stainless steel.

4. The device of claim 1, wherein said base member is coated with an elastomer to frictionally secure said base member to the body.

5. The device of claim 1, wherein the end of each side member extends upwardly from said base plane.

6. The device of claim 1, wherein said cross-members are equally spaced apart.

7. The device of claim 1, wherein said plurality of cross-members extend the entire length of said side members.

8. The device of claim 1, comprising a plurality of brace members.

9. The device of claim 1, wherein said means for securing said device to the body is a waist strap.

10. The device of claim 9, wherein said waist strap is a belt.

11. The device of claim 1, wherein said opening in the body is a congenital orifice.

12. The device of claim 1, wherein said opening in the body is surgically created.

13. The device of claim 12, wherein said opening in the body is an ostomy having a stoma inserted therein with a bag affixed thereto.

14. The device of claim 13, wherein said ostomy is a colostomy.

* * * * *